United States Patent [19]

Jacob

[11] Patent Number: 5,081,043
[45] Date of Patent: Jan. 14, 1992

[54] METHOD AND APPARATUS FOR MULTIELEMENTAL ANALYSIS BY COMBUSTION WITH ELEMENTAL FLUORINE

[75] Inventor: Eberhard Jacob, Tutzing, Fed. Rep. of Germany

[73] Assignee: Man Technologie A.G., Munich, Fed. Rep. of Germany

[21] Appl. No.: 227,345

[22] Filed: Aug. 2, 1988

[30] Foreign Application Priority Data

May 6, 1988 [DE] Fed. Rep. of Germany ....... 3815525

[51] Int. Cl.$^5$ .................... G01N 31/12; G01N 33/20
[52] U.S. Cl. ........................................ 436/73; 436/83; 436/84; 436/124; 436/155; 436/182; 422/68.1; 422/80
[58] Field of Search .............. 436/83, 84, 73, 124, 436/155, 182; 422/80, 68.1

[56] References Cited

U.S. PATENT DOCUMENTS 4,365,969 12/1982 Karpov et al. ................ 436/75

FOREIGN PATENT DOCUMENTS 2101312A 1/1983 United Kingdom .

Primary Examiner—David L. Lacey
Assistant Examiner—David Redding
Attorney, Agent, or Firm—Ladas & Parry

[57] ABSTRACT

For the analysis of a sample in a method capable of wide application, the sample is reacted in a combustion reaction with elementary pure fluorine in a multiple molar excess in relation to the sample in a reactor of pure nickel so that the products of fluorination may be analyzed by spectrometry. A line spectrum can be produced in this manner, for example, from a silicon carbide sample combusted or reacted with elementary fluorine.

14 Claims, 3 Drawing Sheets

FIG.1

METHOD AND APPARATUS FOR MULTIELEMENTAL ANALYSIS BY COMBUSTION WITH ELEMENTAL FLUORINE

BACKGROUND OF THE INVENTION

The invention relates to a multielement analytical method of the type in which a sample of the substance to be analyzed is burned with a reactant and then analyzed.

The most important and quantitative micro- and ultramicromethods for organic materials involving decomposition and separation are based on the combustion of compounds in oxygen at 1,000° to 2,000°. The products of combustion consist of highly volatile oxides ($H_2O$, $CO_2$ and $SO_2$) and elements ($N_2$, $Cl_2$, $Br_2$ and $I_2$) and sparingly volatile or non-volatile oxides (ash). The assay of the readily volatile materials is undertaken sequentially with element-specific methods. $H_2O$, $CO_2$ and $N_2$ (in CHN analysis) are for instance determined simultaneously by gas chromatography, a process which may be also modified for the determination of $SO_2$ as well (S analysis, see E. Pella, B. Colombo, Mikrochim. Acta (Vienna), 1973, pages 697 to 719).

Despite comminution and the use of high temperatures, the combustion of inorganic materials in oxygen is frequently incomplete, since the oxygen compounds formed are mostly non-volatile. Instrumental methods are limited to the determination of the elements hydrogen, carbon and sulfur using two different devices. For determining different concentration ranges several instruments are required. The German patent 3,036,959 describes an extraction method for the volatilisation of the elements to be determined by reaction with non-volatile fluorides and chlorides in a metallic melt under conditions which are experimentally difficult to maintain followed by gas analysis of the volatile halides. Part of the volatile halides described—which are analysed in the gaseous phase—do not exist under the conditions described, and certainly include the hexafluorides $IrF_6$, $MoF_6$, $OsF_6$ $ReF_6$ and $UF_6$, which are reduced to non-volatile, lower fluorides by metals.

Organic materials are fluorinated at 80° C. and the products of such fluorination analyzed by gas chromatography. Owing to their aggressive action of the fluorine and the hydrogen fluoride on the filling material of the separating column, fluorine and hydrogen are removed prior to gas chromatography by absorption. In this method it is possible to use the inert fluorides $CF_4$ and $SF_6$ and the elements oxygen and nitrogen for the determination of carbon, sulfur, oxygen and nitrogen (see K. Asai and D. Ishii, J. Chromatogr. 69 (1972), pages 355/8). The said elements may be determined very much more simply and accurately by oxygen combustion analysis as initially mentioned.

SHORT SUMMARY OF THE INVENTION

One object of the invention is to develop a method for quantitative multielement analysis which is of substantially universal application.

In order to attain this or other objects appearing from the present specification and claims, in the invention the sample of the substance is placed in a reactor with a multiple molar excess of fluorine and reacted therewith at a temperature between 200° C. and 700° C.

The method in accordance with the invention makes possible a quantitative combustion of all organic and element-organic materials even if they are in a compact condition. Thus the method is of universal application and has the additional advantage that it is possible to attain a quantitative conversion into vapor of all non-metals and a series of metals so that it is possible to speak of a universal separation and enrichment method. Furthermore the quantitative gas analysis of the substances converted into vapor, and thus of a selection and testing of methods suitable therefor is possible.

The amount of fluorine is limited to 10 mmol (380 mg). Such a small amount of fluorine may be freely handled without any hazard. The maximum amount of sample depends on the chemical composition thereof and the concentration of the element therein to be determined. The degree of fluorine excess depends on the requirement for quantitative fluorination so that for a given element to be determined there is, as far as possible, only one target compound as will be explained in the examples below.

The combustion with fluorine preferably takes place statically in a reactor of pure nickel and at the said temperature between 200° and 700° C. or more particularly between 250° and 650° C. The optimum temperature will depend on the respective chemical composition of the sample to be analyzed.

It is an advantage if the sample of the substance is in a compact form. In the case of metals such as Ni, Cu and Au, and their alloys and in the case of refractory oxides whose main components form non-volatile fluorides (for instance $Al_2O_3$) it is however best for the sample to be comminuted.

In the case of element-organic compounds the sample may be burned to ash, this leading to an enrichment for trace element analysis.

In accordance with a further possible feature of the invention the fluorine used for fluorination is condensed by cooling the reactor. This prevents uncontrolled ignition during the introduction of the fluorine. If liquid nitrogen is used for cooling, the safety of the procedure is still further increased insofar as fluorine may be taken from a container in which it is held at normal or reduced pressure.

A compact sample of the substance to be analyzed is weighed out in a crucible of pure nickel, magnesium fluoride or calcium fluoride. The crucible may have a diameter of 2 to 3 mm and after placing it in the reactor the contents are spilled by shaking the reactor so that the sample was evenly distributed over the floor of the reactor.

For determination of the non-volatile residue a retrievable crucible with a diameter between 3 and 6.5 mm was placed in a depression in the floor of the reactor and fixed in place.

A suitable amount of fluorine used for fluorination was condensed in the reactor by cooling to −196° with liquid nitrogen. Then the reactor was heated up to the sample-specific temperature. Temperature data are presented in the ensuing examples. The fluorine used for the flourination process has a purity of at least 99.9%. Moreover the oxygen content of the fluorine is to be taken into account in order to prevent falsification of the oxygen determination, and to prevent masking of elements by the formation of dioxygenyl salts.

LIST OF THE FIGURES OF THE DRAWINGS

FIG. 1 shows a table of the elements to indicate the fluorides significant for the invention with varying degrees of volatility.

In the invention it is to be observed that the quantitative conversion into the vapor state of all non-metals and of a series of metals in the form of fluorides takes place. It has been discovered for the first time that the fluorination of elements and compounds with excess fluorine using the method of the invention made possible separation of the elements into two groups with a high separation factor. The table of FIG. 1 lists the products of fluorination which were formed at temperatures between 250° and 650° C.

Figure 3:
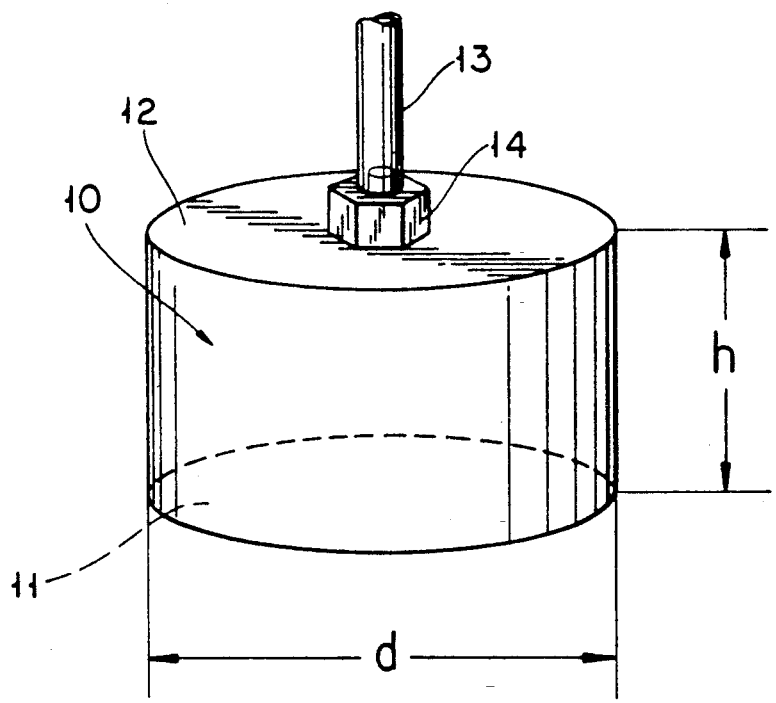
FIG. 3 shows the diameter to height ratio of the cylinder of the reactor.
Figure 4:
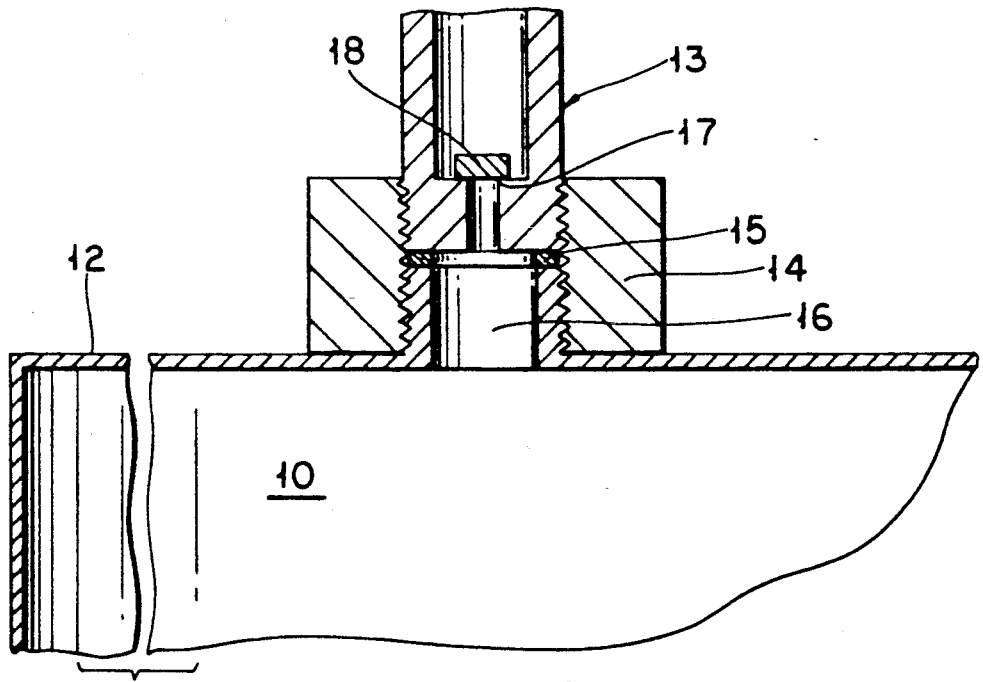
FIG. 4 shows the details of the valve positioned at the top end of the reactor.

For the combustion of a sample with elementary fluorine a reactor of pure nickel with a maximum volume of 10 ml. may be used (see FIG. 3)—having a combustion space 10 in the immediate vicinity of the sample occupying more than 90% and preferably 95% of the reactor volume. This combustion space 10, which is in the form of a cylinder with a flat bottom 11, has a ratio of diameter d to height h of between 1 to 0.2 and 1 to 2 and more especially between 0.5 and 0.8 to 1. At the top end 12 the reactor may be provided with a valve 13 having a moving valve member 18 and a seat 17 both made of a nickel alloy. The dead volume 16 of the valve on the valve seat side may be less than 0.5 ml. and preferably has a value of 0.1 ml. On the reactor side the valve may have a screw 14 of a nickel alloy having a rated width of 1 to 6.5 mm for filling the reactor. The screw may be sealed off by an annular copper gasket 15.

Furthermore the valve and the combustion space may be connected by components forming a diffusion barrier in order to prevent the escape of incompletely fluorinated products from the combustion space. Such components may consist of a tube closed at both ends and with an internal diameter under 3 mm and a copper gasket with a rated width of under 2 mm. The connection may also be by way of a tube with an internal diameter 0.1 to 0.05 mm less than the internal diameter of the tube to be inserted therein.

It was to be seen for the first time that the fluorides of the main group elements in the periodic system might be separated into the non-volatile fluorides of the metals and into the volatile fluorides of the non-metals and semi-metals. With the exception of the fluorides of the semi-metals antimony and bismuth—which have boiling points of 141° and 230° C.—the fluorides of the non-metals are in the form of gas at room temperature. Metallic fluorides are saltlike solids which at temperatures under 250° C. do not have any detectable vapor pressure. The most volatile metal fluoride is $SnF_4$ with a sublimation point of 705° C. At a temperature of 250° C. the minimum separation factor between volatile and non-volatile fluorides is better than $10^9$.

It was furthermore discovered that the fluorination of oxygen and nitrogen containing compounds leads to the quantitative liberation of $N_2$ and $O_2$.

Chlorine and xenon containing compounds are fluorinated to a mixture of a large amount of $ClF_3$ and little $ClF_5$ and in the other case a large amount of $XeF_6$ and a little $XeF_4$. Materials containing elements in the subsidiary groups in the table of the elements may also be separated by way of their fluorides. The fluorides of Sc, Y, La and the rare earth metals, Zr and Hf do not have measurable vapor pressures at 250° C. $TiF_4$, $NbF_5$ and $TaF_5$ have a sublimation point of 285° C. and boiling points of 234° C. and 222° C., respectively. $VF_5$, $MoF_6$, $WF_6$, $TcF_6$, $ReF_7$, $OsF_6$ and $IrF_6$ have boiling and sublimation points under 100° C. Ru, Rh and Pt form moderately volatile pentafluorides and readily volatile hexafluorides which are coexistent. Compounds which are not volatile at 250° C. are the trifluorides of Mn, Fe and Co and the difluorides of Ni, Cu, Zn, Ag, Cd and Hg. $CrF_5$, $MnF_4$ and $AuF_3$ vaporize with partial decomposition. The last named fluorides are thus the only exceptions which do not permit a quantitative separation. The actinoid elements form, with the exception of $UF_6$, $NpF_6$ and $PuF_6$, non-volatile fluorides. $PuF_6$ readily decomposes into non-volatile $PuF_4$.

On cooling down the fluorination mixture it is possible for reactions to take place between the various fluorinated products. This takes place for example between:
oxygen and the fluoride acceptors $AsF_5$, $SbF_5$, $BiF_5$, $NbF_5$ and $TaF_5$ with the formation of dioxygenyl salts $O_2^+ EF_6^6$ salts which are thermally stable at 250° C. In order to eliminate this effect additions of NaF, KF, RbF or CsF are made in a double to triple molar excess (in relation to the interfering element) prior to combustion.
between volatile fluoride acceptors (Lewis acids) and non-volatile fluoride donors (Lewis bases) to nonvolatile saltlike complex compounds, as for instance

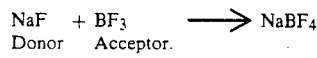
Donor   Acceptor.

Such compounds are thermally decomposed in a vacuum at 500° to 650° C. with a reversal of the reaction leading to their formation.

A further path to the liberation of $BF_3$, $SiF_4$, $GeF_4$, $PF_5$, $AsF_5$ and $BiF_5$ from their complex compounds with fluoride donors is the addition of antimony, niobium or tantalum metal with a double to triple molar excess related to the element fluoride to be liberated. The reaction takes place for instance in accordance with the following equation.

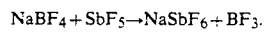

If there is a departure from the optimized fluorination parameters and reaction features in accordance with the invention the efficiency of the method decreases.
Fluorination to produce complex product mixtures with more than two fluorination products from each element,
particularly in the case of the fluorination of carbon containing materials (as for instance carbides) in addition to $CF_4$ as the intended fluoride undesired higher fluorides $C_2F_6$, $C_3F_8$, $i$-$C_4F_{10}$ and neo-$C_5F_{12}$ are produced. In the presence of oxygen $CF_3OF$ is formed and in unfavorable cases even $CF_2(OF)_2$ and $CO_2$,
in the case of the fluorination of nitrogen containing materials it is possible for $NF_4+$ salts to be formed or in the presence of oxygen even $NO^+$ salts (see J. L. Adcock, R. J. Lagow in J. Fluorine Chem. 2 (1972/3) 434/6) or $N_2O$ may be produced. In the case of the fluorination of sulfur containing materials $SO_2F_2$ is produced in the presence of oxygen.

The formation of a mixture impairs determination or renders it impossible.

The subsequent quantitative gas analysis of elements and volatile fluorides is performed by means of Fourier or Hadamard transform vibrational spectrometry (FT or HT-SS).

FT/IR spectrometry

Figure 1:
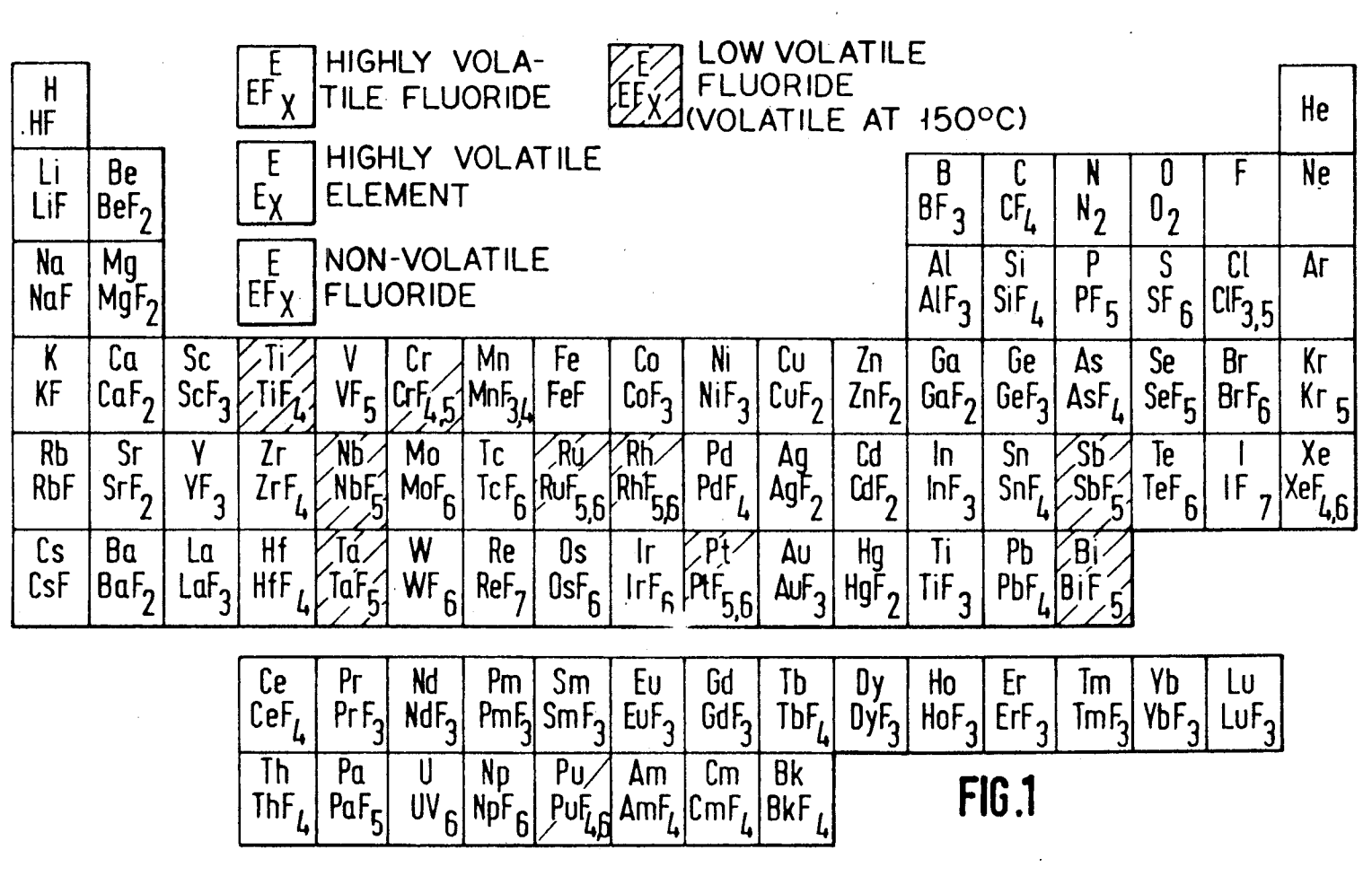

FT/IR gas analysis of the highly volatile fluorides specified in FIG. 1 takes place after expansion of the fluorination mixture at room temperature in an evacuated gas cell with an optical path of at least 150 mm and an optically active volume of 250 ml. at the most. The optically inactive volume of the gas cell and of the supply leads amounted to 10% at the most of the optically active cell content. Preferably cylindrical cells with optical paths of 250 to 500 mm and diameters under 25 mm were used. The cell was held at a given temperature with a thermostat with a variation of $\pm 0.2°$ C. The cell window was in the form of silver chloride (working temperature: 25° to 30° C.) for the range of measurement of 5,000 to 930 cm$^{-1}$. At a working temperature of 150° C. the sparingly volatile fluorides mentioned in FIG. 1 may be determined, if the respective elements are present at the main or subsidiary components. The optically inactive part of the fluorine combustion apparatus is held to with 2° C. of the desired temperature thermostatically. The IR transparency of the elements $F_2$, $N_2$ and $O_2$ is an advantage in the case of fluorine (an excess does not cause an interference), but in the case of $N_2$ and $O_2$ there is a considerable disadvantage since the determination of the elements nitrogen and oxygen is no longer possible.

FT or HT Raman spectrometry with laser excitation

FT/RA or HT/RA gas analysis of the elements and compounds noted in FIG. 1, readily or sparingly volatile fluories after expansion of the fluorination mixture at 150° C. into an evacuated gas cell with an optically active volume of 250 ml. at the most. The material of the cell window is leucosaphir ($\alpha$-$Al_2O_3$). Raman measurement is an advantageous amplification of IR analysis for the determination of $O_2$ and $N_2$.

Mass spectrometry

MS gas analysis of the volatile elements and compounds listed in FIG. 1. The reactor and the inlet part of the spectrometer of pure nickel and nickel alloys is held at a temperature between 100° and 350° C. with an accuracy of $\pm 0.5°$ C. thermostatically. This greatly reduces memory effects and at temperatures over 200° C. the determination of the sparingly volatile elements of FIG. 1 is possible. The possibility of determining the elements oxygen and nitrogen is particularly significant.

EXAMPLES

The present invention will now be further explained with reference to the following examples of analyses.

1. Analysis of ceramic material (a) Boron containing silicon carbide

Figure 2:
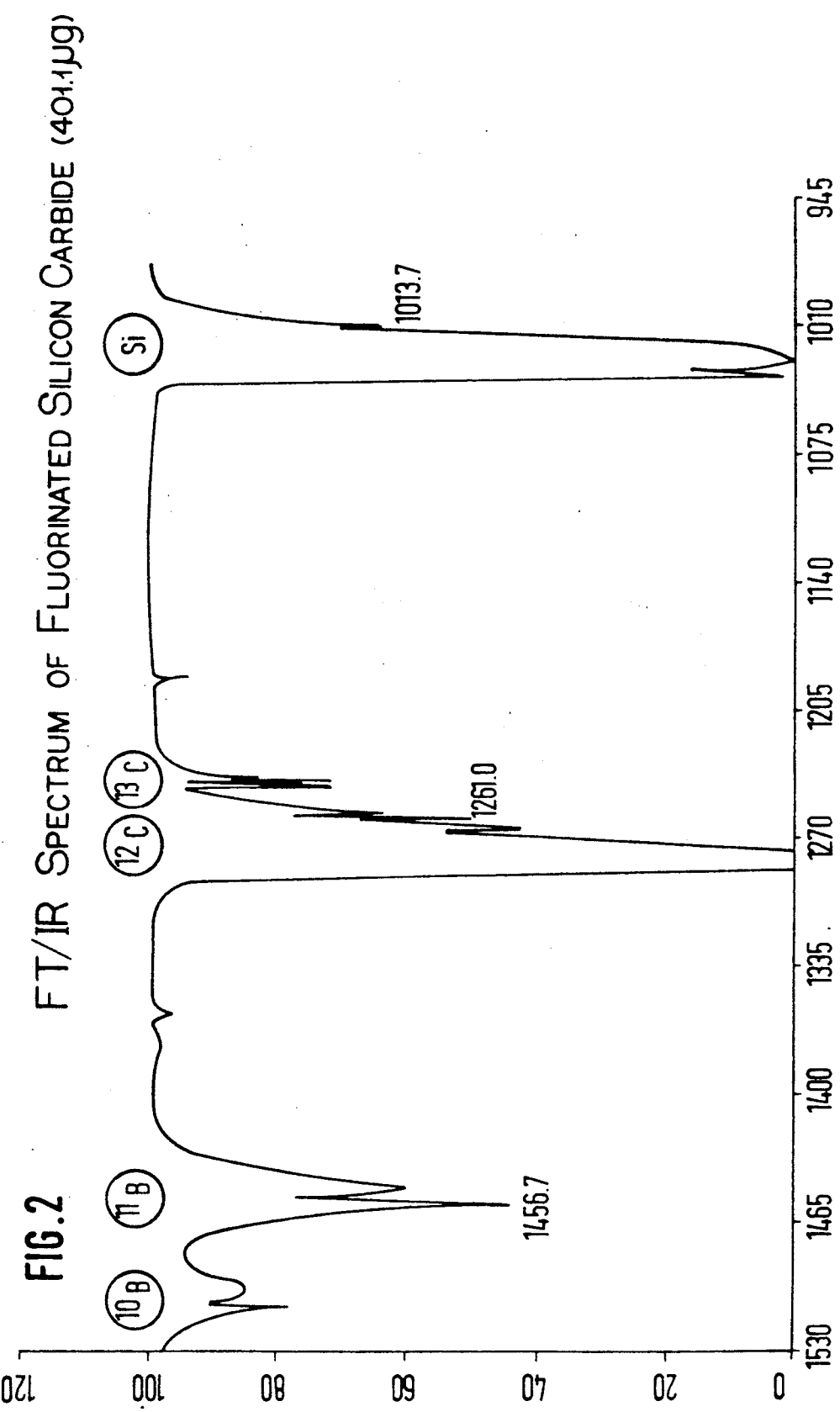
FIG. 2 shows a wavenumber-transmittance curve as an FT IR spectrum in the analysis of fluorinated silicon carbide using the invention.

The material was coarsely comminuted. A fragment weighing approximately 0.4 mg (10 micromol) was weighed on an aultramicrobalance and placed in the fluorine passivated combustion reactor filled with dry $N_2$ or Ar (volume 5 ml.). The reactor was heated for 2 minutes at 550° C. with a vacuum better than $10^{-4}$. After cooling with liquid nitrogen 5 mmol of high purity fluorine were condensed into the reactor at $-196°$ C. The reactor was rapidly heated up to 550° C. and held for 5 minutes at this temperature. After cooling down to $30 \pm 2°$ C. the gaseous content of the reactor was allowed to expand into a silver chloride IR cell thermostatically held at 28° C. The cell had a volume of 125 ml. and an optical length of 300 mm. An FT/IR spectrum was recorded (FIG. 2). In the spectrum it as only possible to see the IR absorption of $BF_3$, $CF_4$ and $SiF_4$, which were formed in accordance with the equations

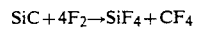
$$SiC + 4F_2 \rightarrow SiF_4 + CF_4$$

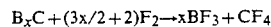
$$B_xC + (3x/2 + 2)F_2 \rightarrow xBF_3 + CF_4$$

(see FIG. 1).

By comparing the measured IR extinctions with calibration charts, which were produced by measuring binary mixtures of $BF_3$, $CF_4$ and $SiF_6$ with fluorine at different fluorine partial pressures, the following results of analysis were achieved:

| –Boron | 5.23 ± 0.05% by weight. |
|---|---|
| Carbon | 31.1 ± 0.1% by weight |
| Silicon | 63.6 ± 0.2% by weight |

Five measurements on different days led to readings within the given error limits. The values are in agreement with the contents of the B,C and Si as set by quantitative synthesis.

(b) Silicon nitride with added yttrium oxide

The material was coarsely comminuted and a fragment of about 1.5 mg (105 micromol) was weighed out with an ultramicrobalance in a nickel crucible having a diameter of 6 mm and a height of 6 mm. The procedure was similar to that of example 1 (a). Fluorination was carried out with high purity fluorine mixed with 0.5% argon. The IR spectrum showed $SiF_4$ as the main component with only traces of HF and $CF_4$.

The analysis was as follows:

| Silicon | 57.2 ± 0.2% by weight |
|---|---|
| Carbon | 800 ± 20 ppm |
| Hydrogen | 350 ± 30 ppm. |

After the FT IR analysis the mixture was examined by mass spectrometry (MS). On the basis of the measured intensity of the peaks at 28 ($N_2^+$), 32 ($O_2^+$) and 40 ($Ar^+$), internal standard) a comparison was performed with calibration curves, which had been prepared with mixtures of $N_2$ and $O_2$ with argon doped fluorine, the following results were obtained:

| Nitrogen | 38.1 ± 0.3% by weight |
|---|---|
| Oxygen | 1.0 ± 0.05% by weight |

A white residue remained in the crucible, which after weighing and dissolving in acid was subjected to IC analysis. The main component was yttrium with traces of aluminum, calcium and iron (in all 300 ppm). Accordingly the fluorination residue consisted of yttrium fluoride with traces of $AlF_3$, $CaF_2$ and $FeF_3$ so that the yttrium content could be worked out as Yttrium $3.73 \pm 0.08\%$ by weight.

The result of this analysis is in agreement with the original weighed out quantities used in the synthesis of the ceramic sample. The quantities of fluorination products found and those expected in accordance with FIG. 1 are identical.

Boron nitride powder

About 1.5 mg (60 micromols) of powder were weighed out in a nickel crucible with a diameter of 3 mm and a height of 3 mm. The crucible was placed in the reactor and the latter shaken in order to distribute the powder onto the bottom of the reactor. The procedure was as in example (1b). The IR spectrum showed $BF_3$ as the main component with traces of HF, $CF_4$ and $SiF_4$.

|  |  | Wavenumber (cm$^{-1}$) |
|---|---|---|
| Boron | 42.5 ± 0.1% by weight | 1456.7 |
| Hydrogen | 1200 ± 200 ppm | 4038.9 |
| Carbon | 320 ± 50 ppm | 1283.0 |
| Silicon | 850 ± 100 ppm | 1029.3 |

The accuracy of determination of trace elements may be markedly improved by increasing the amount weighed out to 15 mg. However, traces of undesired $NF_3$ are then formed.

After the FT IR analysis the gas mixture was subjected to mass spectrometry. On the basis of the intensity of the peaks at 28 ($N_2^+$), 32 ($O_2^+$) and 40 ($Ar^+$) the following results were worked out:

| Nitrogen | 56.4 ± 0.5% by weight |
|---|---|
| Oxygen | 3250 ± 200 ppm |

Performance of analyses with departures from the features of the invention:

If the above mentioned analytical procedures are carried out with a thirty-fold increase in the amounts of sample weighed out, the accuracy of the method may suffer considerably.

In the case of the fluorination of SiC (1a) a few percent of $C_2F_6$ and small amounts of higher fluoroalkanes are formed in addition to the intended fluoride $CF_4$. This renders accurate determination of carbon impossible.

When fluorinating BN (see part 1b) $NF_3$, $N_2O$, $CF_3OF$ and $NO^{30} BF_4^-$ are formed as undesired by-products, which reduce the accuracy of determination of nitrogen, oxygen, carbon and boron to a pronounced extent.

Fluorination of $Si_3N_4$ (1c) is not complete and $NF_3$ is formed as a byproduct.

If the above analytical procedures are carried out with a cylindrical reactor with a volume of 15 ml. and with a diameter to height ratio of the combustion space of 1 to 10 or if the temperature is less that 450° C. similarly unsatisfactory results to those mentioned above will be produced.

2 Analysis of semiconductors (a) Determination of boron and phosphate in silicon Si was coarsely comminuted and a fragment with an approximate weight of 56 mg (2 mmol) was weighed on a microbalance and placed in the fluorine passivated, argon filled combustion reactor (with a volume of 10 ml.). After evacuation and baking (see example 1a) 6 mmols of high purity fluorine were condensed into the reactor. The sample was fluorinated at 250° C. for 5 minutes. The fluorination of the silicon took place according to the reaction $$Si + 2F_2 \rightarrow SiF_4.$$

The mixture resulting from fluorination was then allowed to expand into a nickel cell with $CaF_2$ windows which was held thermostatically at 100° C. The boron content was determined by measurement of extinction of the $BF_3$ band at 1,456.7 cm$^{1-}$. The spectral resolution of the FT IR spectrometer amounted to $<0.5$ cm$^{-1}$. The boron content was found by comparison with standard samples to be $7.0 \pm 0.2$ ppm.

Although the determination of boron and phosphorus may be undertaken at 30° C. in an AgCl cell, there are then memory effects which increase the standard deviation by one order of magnitude. Phosphorus determination is more accurate by mass spectrometry.

After the fluorination expansion of the mixture was allowed to take place into the MS inlet system (150° C.) and the intensity of the $PF_5^+$ peak was measured at 126 ME and that of the $PF_4^+$ was measured at 107 ME. Boron determination is interfered with by coincidence of $^{11}BF_2^+$ with $^{30}SiF^+$ at mass 49.

(b) Silicon determination in gallium arsenide

GaAs was coarsely comminuted. A fragment of approximately 145 mg (1 mmol) was fluorinated with 7 mmol $F_2$ in a manner similar to that of described in part 2a supra, and the gaseous products were investigated by IR spectroscopy in the heated $CaF_2$ cell. By way of the extinction of the $^{28}SiF_4$ band at 1,029.3 cm$^{-1}$ the Si content was determined as $22.2 \pm 0.4$ ppm The fluorination reaction of GaAs is $$GaAs + 3F_2 \rightarrow [GaF_3] + AsF_5.$$

3. Analysis of metallic materials

Determination of non-metals and molybdenum in austenitic chrome-nickel steel 50 mg of steel powder (with a grain size of 10 to 30 microns) were fluorinated in a 5 ml. reactor with 5 mols of high purity fluorine (under conditions similar to part 1a). In the IR spectrum the absorption bands of $CF_4$ (1,283.0), $SiF_4$ (1,029.6), $PF_5$ (946.5) and $MoF_6$ (741.4 cm$^{-1}$) were used for determination of the corresponding elements.

Results: 0.102% C, 2.23% Si, 0.044% P and 2.15% Mo. There was an agreement of ±5% with the manufacturer's data.

I claim:

1. A method for the multielement analysis of a sample in which the sample is combusted with elemental fluorine with a purity of at least 99.9% and volatile fluorides produced from such combustion are analyzed, said fluorine being present in a multiple molar excess of the order of forty fold or more in relation to the amount of sample, said combustion taking place in a reactor at a temperature between 200° C. and 700° C.

2. The method as claimed in claim 1 wherein the amount of said elemental fluorine is limited to essentially 10 mmols.

3. The method as claimed in claim 1 wherein said combustion with the elemental fluorine takes place statically in the reactor consisting essentially of pure nickel.

4. The method as claimed in claim 1 wherein the sample is placed in a compacted form in the reactor.

5. The method as claimed in claim 1 wherein the reactor is cooled to at least −150° C. prior to the addition of the fluorine.

6. The method as claimed in claim 1 wherein for the avoidance of an interfering effect in the presence of an element selected from the group consisting essentially of arsenic, antimony, bismuth, niobium and tantalum an addition of a fluorine compound selected from the group consisting essentially of NaF, RbF and CsF is made in a metered quantity prior to said combustion.

7. The method as claimed in claim 1 wherein for the avoidance of an interfering effect in the presence of an element selected from the group consisting essentially of sodium, potassium, rubidium and cesium an element selected from the group consisting essentially of antimony, niobium and tantalum in an elementary form is added in a metered quantity prior to said combustion.

8. The method as claimed in claim 1 wherein said analysis step comprises flowing said volatile fluorides into a gas cell held at a thermostatically controlled temperature between 25° C. and 250° C. and being spectrometrically analyzed.

9. The method as claimed in claim 8 wherein said gas cell has a cell window comprising a chloride selected from the group consisting of silver chloride and calcium fluoride.

10. The method as claimed in claim 1 wherein said analysis of said volatile fluorides is performed with a mass spectrometer at a temperature between 30° C. and 350° C.

11. A reactor for performing analysis of a sample by reacting the sample with elemental fluorine, said reactor consisting essentially of pure nickel comprising a combustion space for said reaction with fluorine equal to at least 90% of the reactor volume, said combustion space being in the form of a cylinder with a flat bottom and with a diameter to height ratio of between 1 to 0.2 and 1 to 2.

12. The reactor as claimed in claim 11 wherein said reactor volume is equal to about 10 ml.

13. The reactor as claimed in claim 11 comprising a valve at an upper end of said cylinder, said valve consisting essentially of a nickel alloy and constructed so as to have a dead volume on its valve seat side less than 0.5 ml.

14. The reactor as claimed in claim 13 wherein on a side of said valve adjacent said reactor, said valve has a nickel alloy screwplug for filling said reactor, said plug comprising a copper gasket ring.

* * * * *